(12) United States Patent
Loo et al.

(10) Patent No.: US 11,744,449 B2
(45) Date of Patent: Sep. 5, 2023

(54) ENDOSCOPY SYSTEM

(71) Applicant: ALTEK BIOTECHNOLOGY CORPORATION, Hsinchu (TW)

(72) Inventors: Hsi-Hsin Loo, Taipei (TW); Chun-Wei Liu, Hsinchu County (TW); Liang-Yi Li, Hsinchu County (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 262 days.

(21) Appl. No.: 17/089,733

(22) Filed: Nov. 5, 2020

(65) Prior Publication Data
US 2021/0298588 A1 Sep. 30, 2021

(30) Foreign Application Priority Data

Mar. 27, 2020 (TW) .................................. 109110610

(51) Int. Cl.
*A61B 1/12* (2006.01)
*H05K 1/02* (2006.01)
(Continued)

(52) U.S. Cl.
CPC .......... *A61B 1/128* (2013.01); *A61B 1/00066* (2013.01); *A61B 1/00121* (2013.01);
(Continued)

(58) Field of Classification Search
CPC . A61B 1/128; A61B 1/00066; A61B 1/00121; A61B 1/015; H05K 1/0203; H05K 1/028; H05K 7/20272; H05K 7/2039
See application file for complete search history.

(56) References Cited

U.S. PATENT DOCUMENTS 5,647,871 A * 7/1997 Levine ............... A61B 18/1442
606/49
8,622,894 B2 1/2014 Banik et al.
(Continued)

FOREIGN PATENT DOCUMENTS

CN 101518436 9/2009
CN 101660733 3/2010
(Continued)

OTHER PUBLICATIONS

Machine Translation CN 104337490 A, Jung, Hu, Liu, Huang, Feb. 11, 2015.*
(Continued)

*Primary Examiner* — Aaron B Fairchild
*Assistant Examiner* — Julianna J Nicolaus
(74) *Attorney, Agent, or Firm* — JCIPRNET

(57) ABSTRACT

An endoscopy system including an insertion tube segment, a handle segment, at least one heat source, a heat pipe and a heat-conductive material is provided. The insertion tube segment has first and second end portions opposite to each other and is inserted in the handle segment. An inside of the insertion tube segment and an inside of the handle segment commonly have a connecting space. The at least one heat source is disposed in the first end portion. The heat pipe is disposed in the connecting space and at least extends from a portion of the connecting space of the insertion tube segment to a portion of the connecting space of the handle segment. The heat-conductive material is disposed between the at least one heat source and the first end portion, and the heat-conductive material is thermally coupled to the at least one heat source and the heat pipe, respectively.

19 Claims, 15 Drawing Sheets

(51) Int. Cl.
*A61B 1/00* (2006.01)
*H05K 7/20* (2006.01)
*A61B 1/015* (2006.01)

(52) U.S. Cl.
CPC ........... *A61B 1/015* (2013.01); *H05K 1/0203* (2013.01); *H05K 1/028* (2013.01); *H05K 7/2039* (2013.01); *H05K 7/20272* (2013.01)

(56) References Cited

U.S. PATENT DOCUMENTS

| | | | |
|---|---|---|---|
| 9,510,744 B2 | 12/2016 | Schrader et al. | |
| 2005/0070048 A1* | 3/2005 | Tolchinsky | H01L 23/3735 |
| | | | 257/E23.09 |
| 2011/0306834 A1 | 12/2011 | Schrader et al. | |
| 2014/0364694 A1* | 12/2014 | Avron | A61B 1/00137 |
| | | | 600/164 |
| 2015/0230821 A1* | 8/2015 | Batchelor | A61B 17/32002 |
| | | | 606/180 |
| 2015/0297069 A1* | 10/2015 | Coppersmith | A61B 1/0676 |
| | | | 600/249 |
| 2015/0316245 A1 | 11/2015 | Wong et al. | |
| 2015/0335233 A1* | 11/2015 | Pilz | A61B 1/00128 |
| | | | 600/101 |
| 2016/0235285 A1* | 8/2016 | Shirota | A61B 1/07 |
| 2018/0132889 A1 | 5/2018 | Batchelor et al. | |
| 2019/0056583 A1 | 2/2019 | Kuhn et al. | |

FOREIGN PATENT DOCUMENTS

| | | |
|---|---|---|
| CN | 103874450 | 6/2014 |
| CN | 104337490 | 2/2015 |
| CN | 205249677 | 5/2016 |
| CN | 109414250 | 3/2019 |
| TW | 201519848 | 6/2015 |
| TW | 201919537 | 6/2019 |
| TW | 201936111 | 9/2019 |

OTHER PUBLICATIONS

Machine Translation CN 205249677, Yu, May 18, 2016.*
"Office Action of China Counterpart Application", dated Aug. 1, 2022, pp. 1-10.
"Office Action of China Counterpart Application", dated Dec. 26, 2022, p. 1-p. 8.

* cited by examiner

ENDOSCOPY SYSTEM

CROSS-REFERENCE TO RELATED APPLICATION

This application claims the priority benefit of Taiwan patent application serial no. 109110610, filed on Mar. 27, 2020. The entirety of the above-mentioned patent application is hereby incorporated by reference herein and made a part of this specification.

BACKGROUND

Technical Field

The disclosure relates to an endoscopy system.

Description of Related Art

With the technological progress in semiconductors and micromachines, the application of video endoscopes is becoming more and more popular. Compared with complex optical systems of traditional optical endoscopes, simplified structures of the video endoscopes make it possible to further miniaturize endoscopes. The sizes of the endoscopes are not only reduced, but the resolution and image quality are also improved. In addition, configuring the image sensors and illumination devices towards the front ends of the endoscopes has become a trend of system development.

Due to the concentration of electronic components towards the front ends, the image sensors, the illuminating devices and related parts generate heat during operation. Moreover, the integration density is also increased. As a result, the tissues and organs of the human body may be at hazard due to high temperature of the distal end of the tip part. In order to make the temperature meet the requirements of relevant laws and regulations, heat management and heat dissipation countermeasures will become more and more important as the efficiency of image systems improves.

SUMMARY

The invention provides an endoscopy system which has a good heat dissipation effect.

An embodiment of the invention provides an endoscopy system which includes an insertion tube segment, a handle segment, at least one heat source, a heat pipe, and a heat-conductive material. The insertion tube segment has a first end portion and a second end portion which are opposite to each other. The insertion tube segment is inserted into the handle segment. An inside of the insertion tube segment and an inside of the handle segment commonly have a connecting space. The at least one heat source is disposed at the first end portion of the insertion tube segment. The heat pipe is disposed in the connecting space, and at least extends from a portion of the connecting space of the insertion tube segment to a portion of the connecting space of the handle segment. The heat-conductive material is disposed between the at least one heat source and the first end portion of the insertion tube segment, and is thermally coupled to the at least one heat source and the heat pipe respectively.

In one embodiment of the invention, the handle segment further includes a front end portion and a grip portion. The front end portion clamps the second end portion of the insertion tube segment, and the front end portion is positioned between the insertion tube segment and the grip portion.

In one embodiment of the invention, the heat pipe only extends from a portion of the connecting space of the insertion tube segment to a portion of the connecting space of the front end portion.

In one embodiment of the invention, the endoscopy system further includes another heat-conductive material. The other heat-conductive material is disposed in a portion of the connecting space of the front end portion and is positioned between the front end portion and the heat pipe.

In one embodiment of the invention, in the connecting space of the front end portion, a medium between the heat pipe and the front end portion is air.

In one embodiment of the invention, an appearance of the front end portion includes a cooling fin structure.

In one embodiment of the invention, the heat pipe extends from a portion of the connecting space of the insertion tube segment, through a portion of the connecting space of the front end portion, to a portion of the connecting space of the grip portion.

In one embodiment of the invention, in the connecting space of the grip portion, the medium between the heat pipe and the grip portion is air.

In one embodiment of the invention, the endoscopy system further includes a heat sink disposed in the connecting space of the grip portion and positioned between the heat pipe and the grip portion.

In one embodiment of the invention, the endoscopy system further includes a water cooling system disposed in the connecting space of the grip portion and communicates with the outside, and the water cooling system is thermally coupled to the heat sink and the grip portion respectively.

In one embodiment of the invention, the at least one heat source is an electronic functional element.

In one embodiment of the invention, one of the at least one heat source includes a flexible printed circuit, the flexible printed circuit further includes an extending portion and a covering portion, the extending portion at least extends from a portion of the connecting space of the first end portion of the insertion tube segment to a portion of the connecting space of the connecting portion of the insertion tube segment, the covering portion is disposed on the extending portion, and the extending portion and the covering portion commonly cover the heat pipe.

In one embodiment of the invention, one of the at least one heat source includes a flexible printed circuit, and the flexible printed circuit further includes an extending portion, and the extending portion at least extends from a portion of the connecting space of the first end portion of the insertion tube segment to a portion of the connecting space of the connecting portion of the insertion tube segment.

In one embodiment of the invention, the heat-conductive material includes a heat-conductive adhesive or heat-conductive paste.

In one embodiment of the invention, the endoscopy system further includes a protective element disposed at the first end portion of the insertion tube segment and configured to cover the at least one heat source.

In one embodiment of the invention, the endoscopy system further includes an insulator disposed in a portion of the connecting space in the insertion tube segment and covering the at least one heat source and the heat pipe.

In one embodiment of the invention, the material of the handle segment includes metal, a high-heat-conductive material or a combination thereof.

Based on the foregoing, in the endoscopy system of the embodiment of the invention, since the heat sources are disposed at the first end portion of the insertion tube segment, the heat-conductive material is disposed between the first end portion and the heat sources and thermally coupled to the heat pipe in such a manner that the heat pipe extends from the connecting space in the insertion tube segment to the connecting space of the handle segment. When the heat sources radiate heat due to the execution of the function of the heat sources, the heat can be quickly transferred to the heat pipe by the heat-conductive material, and the heat can be guided from the first end portion of the insertion tube segment which is closer to a patient to the handle segment further away from the patient, and besides achievement of a rapid heat dissipation effect, influences of heating of the heat sources to the patient can be reduced.

DESCRIPTION OF THE EMBODIMENTS

Figure 1:
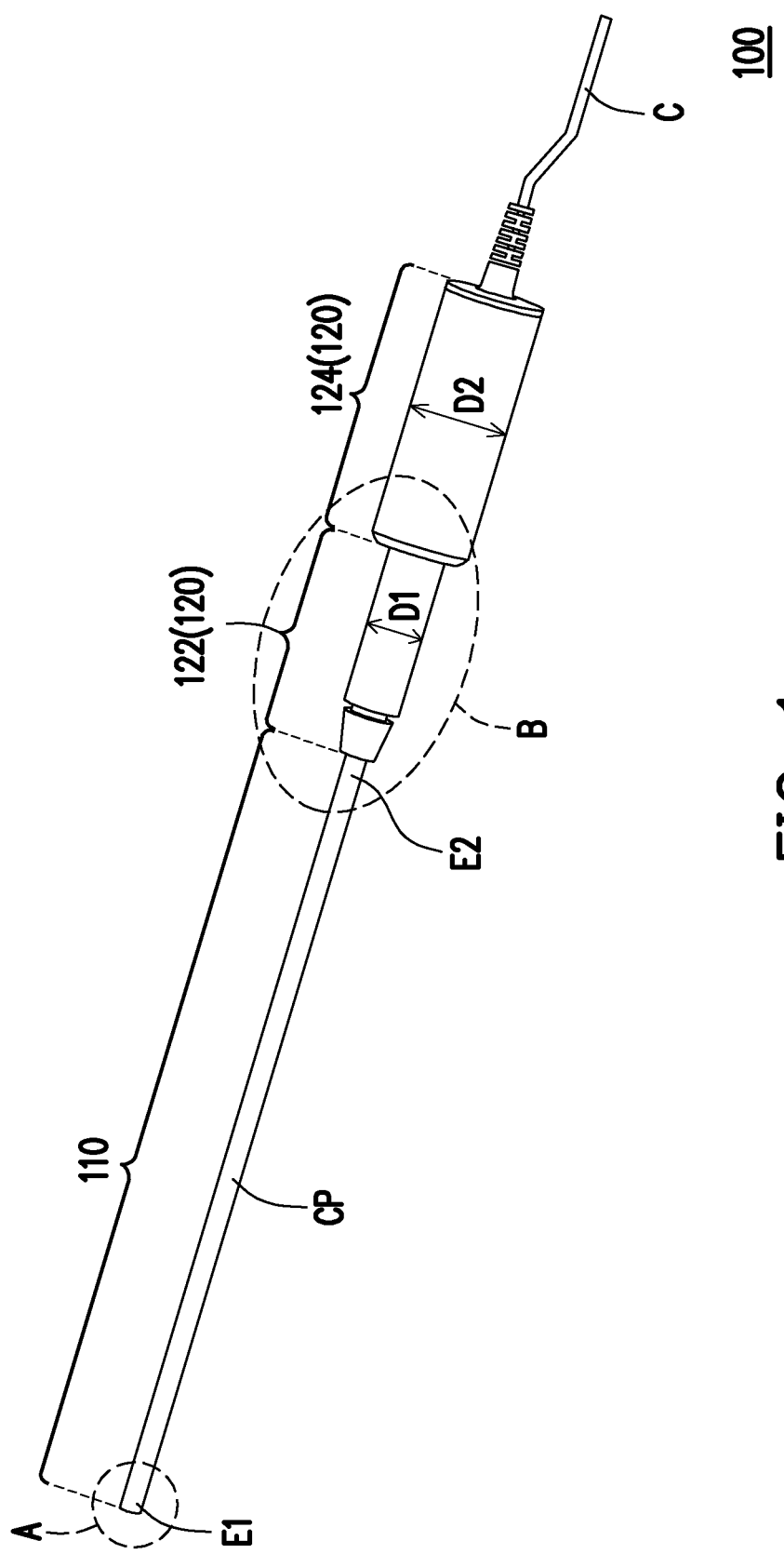
FIG. 1 is a schematic diagram of the appearance of an endoscopy system in accordance with one embodiment of the invention.
Figure 2A:
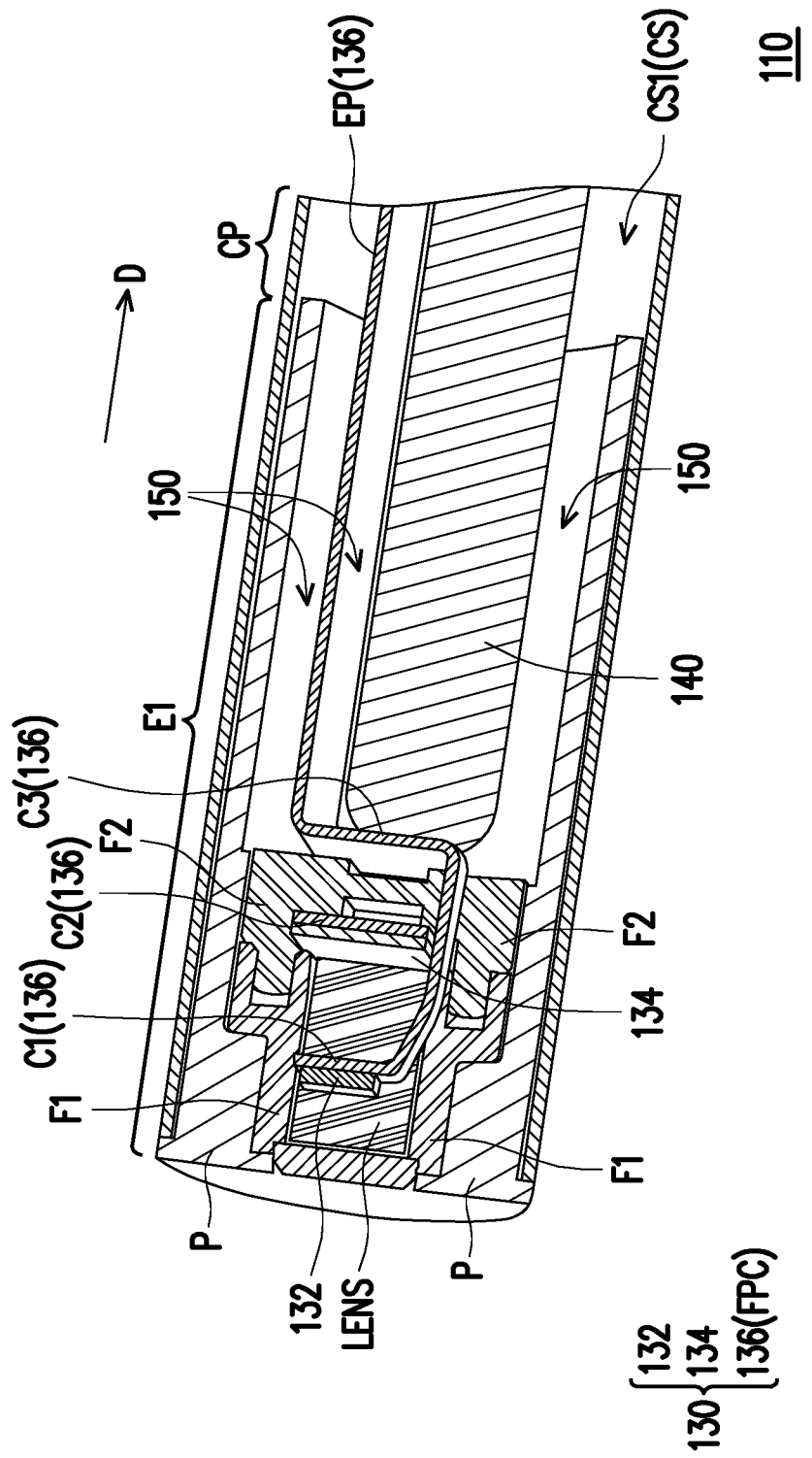
FIG. 2A is a schematic cross-sectional view of a circle A in FIG. 1.
Figure 2B:
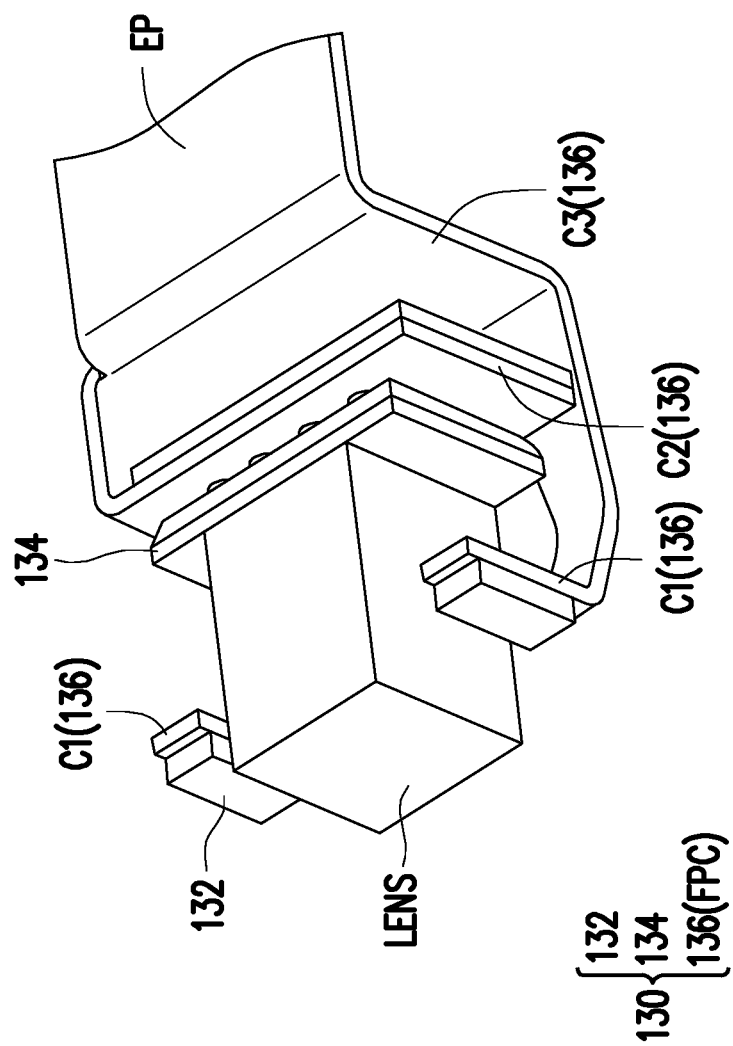
FIG. 2B is a schematic structural diagram of a plurality of heat sources in FIG. 1A.
Figure 3A:
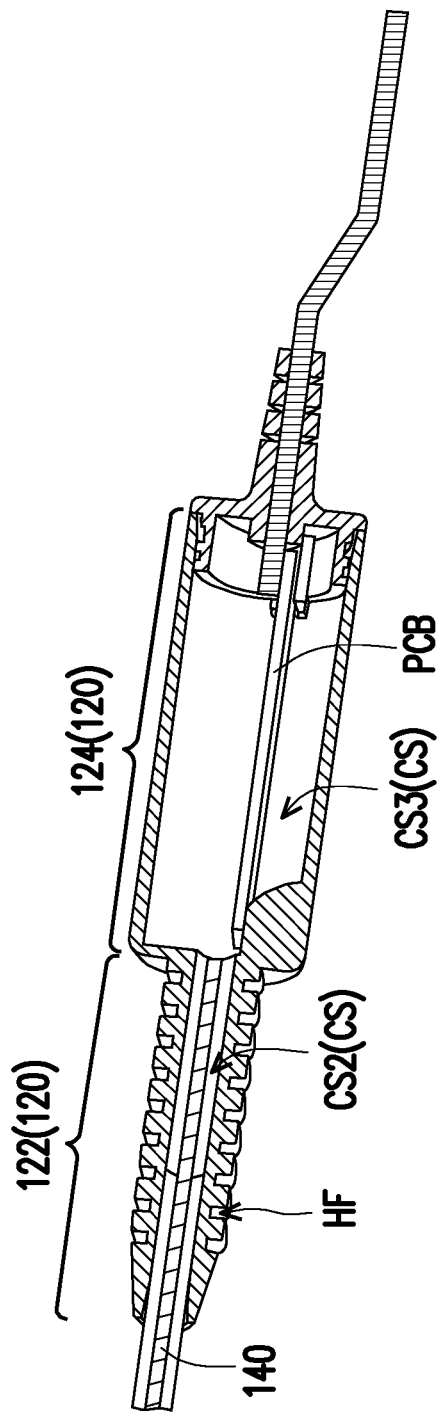
FIG. 3A to FIG. 3F are schematic cross-sectional views of different embodiments of a circle B in FIG. 1.

FIG. 1 is a schematic diagram of the appearance of an endoscopy system in accordance with one embodiment of the invention. FIG. 2A is a schematic cross-sectional view of a circle A in FIG. 1. FIG. 2B is a schematic structural diagram of a plurality of heat sources of FIG. 1A. FIG. 3A is a schematic cross-sectional view of one embodiment of a circle B in FIG. 1.

Referring to FIG. 1, FIG. 2A and FIG. 3A, in the present embodiment, the endoscopy system 100 includes an insertion tube segment 110, a handle segment 120, at least one heat source 130, a heat pipe 140, a heat-conductive material 150 and a protective element P. The elements and the arrangements between the elements are described in detail in the following paragraphs.

The material of the insertion tube segment 110 includes, for example, but is not limited to, a high-heat-conductive material including, for example, metal and, for example, stainless steel. The insertion tube segment 110 has a first end portion E1 and a second end portion E2 which are opposite to each other as well as a connecting portion CP positioned between the first end portion E1 and the second end portion E2, where the connecting portion CP is connected with the first end portion E1 and the second end portion E2.

The handle segment 120 is a mechanism for controlling movement of the insertion tube segment 110. A user may indirectly control parameters such as the manner of movement, angle of rotation and position of the first end portion E1 of the insertion tube segment 110 by applying a force to the handle segment 120. As shown in FIG. 1, in the present embodiment, the handle segment 120 includes a front end portion 122 and a grip portion 124. The front end portion 122 clamps the second end portion E2 of the insertion tube segment 110, and the front end portion 122 is positioned between the grip portion 124 and the insertion tube segment 110, where the diameter D1 of the front end portion 122 is different (for example, smaller than) from the diameter D2 of the grip portion 124. In other embodiments not shown, the diameters D1 and D2 may also be the same and the invention is not limited thereto. In addition, in the present embodiment, the handle segment 120 may be made, for example, of a high-heat-conductive material, such as metal, a high-heat-conductive plastic or a combination thereof, to accelerate heat dissipation. However, in other embodiments, if the heating power of the heat sources 130 is low, the material of the handle segment 120 may be selected to be general plastic to reduce manufacturing costs, and the invention is not limited thereto.

Heat sources 130 are electronic functional elements specifically, such as electronic elements that can perform their corresponding electronic function to generate heat, or an element that is susceptible to heat generation during operation is also considered a heat source. Referring to FIG. 2A and FIG. 2B, and in particular, the number of heat sources 130 is multiple and, for example, three. These heat sources 130 are referred to as a first heat source 132, a second heat source 134 and a third heat source 136. These heat sources 130 are all disposed at the first end portion EP of the insertion tube segment 110. The electronic functions of these three heat sources are described in the following paragraphs respectively.

In detail, the first heat source 132 is, for example, a light emitting element that may be used to emit light, such as, but not limited to, a light emitting diode (LED), for example, to emit a light beam to illuminate the interior of a patient. In the present embodiment, the number of the first heat sources 132 is, for example, two. In other embodiments, the number of the first heat sources 132 may be, for example, one, two or more than two (for example, six), and one of ordinary skill in the art may correspondingly arrange a different number of light emitting elements according to lighting requirements.

The second heat source 134 is, for example, an image sensor of an imaging device, where the image sensor is, for example, a complementary metal-oxide-semiconductor (CMOS); the CMOS image sensor is referred to for short, but not limited thereto, and the image sensor is further optically coupled to a lens of the imaging device. When the first heat source 132 (light emitting diode) emits a light beam to irradiate the patient, a reflected light beam from the interior of the patient enters the insertion tube segment 110 from the first end portion E1, and the reflected light beam is received by the lens to form an image on the image sensing surface of the second heat source 134 (image sensor), so that the image sensor senses the image.

The third heat source 136 is, for example, but not limited to, a circuit carrier board and electronic components thereon, and is, for example, a flexible printed circuit (FPC). More specifically, the FPC further includes a first carrying portion C1, a second carrying portion C2, a third carrying portion C3 and an extending portion EP, where the first carrying portion C1 is a carrying portion closest to an opening (not shown)

of the first end portion E1, the second carrying portion C2 is a carrying portion closer to the opening, the third carrying portion C3 is a carrying portion furthest from the opening, and the first carrying portion C1, the second carrying portion C2 and the third carrying portion C3 are connected with one another, and the extending portion EP is connected to the third carrying portion C3. Referring to FIG. 2A and FIG. 2B at the same time, the first carrying portion C1 carries the first heat source 132 (light emitting element). The second carrying portion C2 carries a fixing seat F1, the second heat source 134 (image sensor) and the lens, and the second heat source 134 (image sensor) and the lens are disposed in the fixing seat F1. A fixing seat F2 of the flexible circuit printed (FPC) is disposed between the second carrying portion C2 and the third carrying portion C3. The extending portion EP extends out of the first end portion E1 from the first end portion E1 towards the direction D of the connecting portion CP.

It is to be noted that the fixing seat F1 is used for fixing the lens and the first heat source 132 (light emitting element), and the fixing seat F2 of the flexible printed circuit (FPC) is used for fixing the flexible printed circuit (FPC), and the materials of the fixing seats F1 and F2 may be heat-conductive plastic or metal materials so as to further guide out the heat generated by the heat sources 130 in an accelerated manner, where the coefficient of heat conduction of the heat-conductive plastic, for example, falls within the range of 0.3-20 W/mK, and the invention is not limited thereto.

The heat pipe 140 is a heat-conductive element having good heat conductivity. In the present embodiment, the inside of the insertion tube segment 110 and the inside of the handle segment 120 commonly have a connecting space CS, where the connecting space of the insertion tube segment 110 is marked as CS1, the connecting space of the front end portion 122 is marked as CS2, and the connecting space of the grip portion 124 is marked as CS3. Referring to FIG. 2A and FIG. 3A, the heat pipe 140 is disposed in the connecting space CS, and the heat pipe 140 extends from the connecting space CS1 of the insertion tube segment 110 to the connecting space CS2 of the front end portion 122, but does not extend to the connecting space CS3 of the grip portion 124. By not extending the heat pipe 140 to the connecting space CS3 in the grip portion 124, a printed circuit board (PCB) in the grip portion 124 can be prevented from generating heat to affect the heat dissipation capability of the heat pipe 140. In the present embodiment, the diameter of the heat pipe 140 is, for example, falls within the range of 1.5 millimeters to 6 millimeters, and the length is, for example, falls within the range of 150 millimeters to 300 millimeters, but the invention is not limited thereto.

The heat-conductive material 150 is a material having good heat conductivity, such as a heat-conductive adhesive or heat-conductive paste, but the invention is not limited thereto. Referring to FIG. 2A, the heat-conductive material 150 is disposed between the at least one heat source 130 and the first end portion E1 of the insertion tube segment 110, and the heat-conductive material 150 is thermally coupled to the heat pipe 140. Since the heat-conductive material 150 is arranged in the space between the heat sources 130 and the insertion tube segment 110, from another viewpoint that the heat-conductive material 150 occupies the space occupied by air having poor heat conductivity, and the heat generated by the heat sources 130 can be guided out of the insertion tube segment 110 in an accelerated manner.

The protective element P is, for example, an internal element capable of providing a protective function to the endoscopy system 100. The material of the protective element includes, for example, polycarbonate (PC) or other light-transmitting material, but the invention is not limited thereto. The protective element P is disposed at the first end portion E1 of the insertion tube segment 110 and is configured to cover at least one heat source 130 to provide a protective function for the heat sources 130. In addition, the protective element P further includes a light guide element for guiding the light beam emitted by the light emitting element (the first heat source 132), and the light guide element may be disposed at the downstream of the light path of the light emitting element, so that the irradiation effect of the light emitting element may be further improved.

As described above, in the endoscopy system 100 of the present embodiment, since the heat sources 130 are disposed near the first end portion E1 close to the patient, the heat-conductive material 150 is disposed between the first end portion E1 and these heat sources 130 and is thermally coupled to the heat pipe 140, the heat pipe 140 is disposed to extend from the connecting space CS1 in the insertion tube segment 110 to the connecting space CS3 of the front end portion 122 via the connecting space CS2 of the front end portion 122. Therefore, when the heat sources 130 radiate heat by performing the functions thereof, the heat can be rapidly transferred to the heat pipe 140 by the heat-conductive material 150, and the heat can be guided from the first end portion E1 of the insertion tube segment 110 closer to the patient to the front end portion 122 further from the patient, and besides achievement of a rapid heat dissipation effect, the influences of the heat on the patient can be reduced.

Furthermore, it is worth mentioning that, provided that the power of these heat sources 130 is small, it is possible to dissipate heat in the heat pipe 140 at a position further away from the first end portion EP1 without having to be externally connected to other heat dissipation structures.

It must be explained here that the following embodiments follow part of contents of the foregoing embodiment, and omit the description of the same technical contents, and reference may be made to the part of the contents of the foregoing embodiment with respect to the same element names, and the descriptions thereof are omitted in the following embodiments.

FIG. 3B to FIG. 3F are schematic cross-sectional views of different embodiments of a circle B in FIG. 1.

Figure 3B:
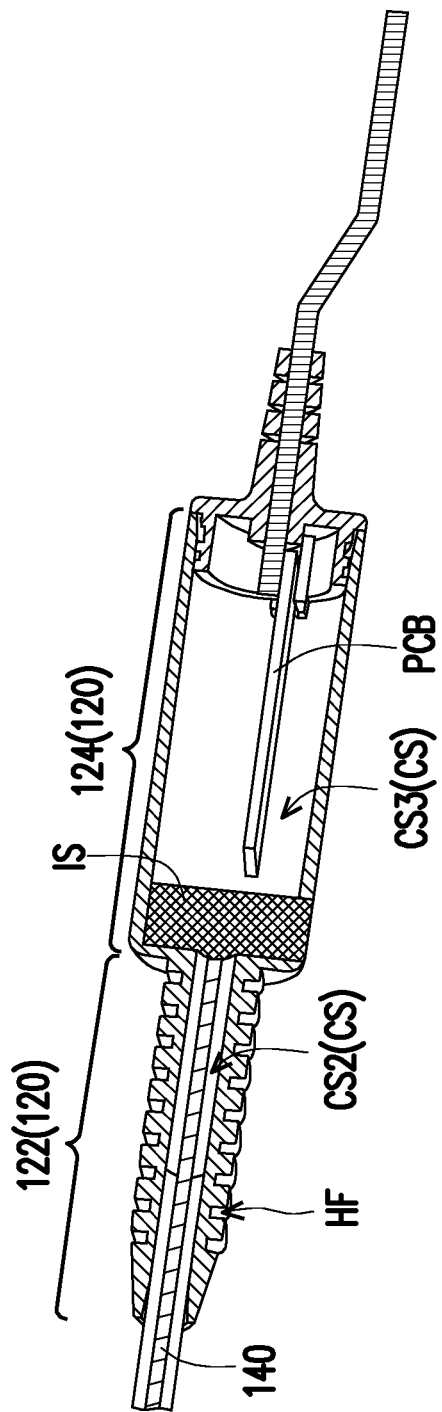

Referring to FIG. 3B, the embodiment is substantially similar to the embodiment of FIG. 3A, the main difference between the embodiment of FIG. 3B and the embodiment of FIG. 3A is as follows: the endoscopy system 100 may optionally include a thermal insulator IS. The thermal insulator IS is disposed between a portion of the connecting space CS2 of the front end portion 122 and a portion of the connecting space CS3 of the grip portion 124. Due to the fact that the heat generated by the printed circuit board (PCB) affects the heat pipe 140 through air if the thermal insulator is not disposed, heat conduction between the connecting space CS2 and the connecting space CS3 can be insulated through the arrangement of the thermal insulator IS, and the heat dissipation effect of the heat pipe 140 can be prevented from being affected. In the present embodiment, the material of the thermal insulator IS is, for example, foam or other suitable material having low heat conductivity, but the invention is not limited thereto.

Figure 3C:
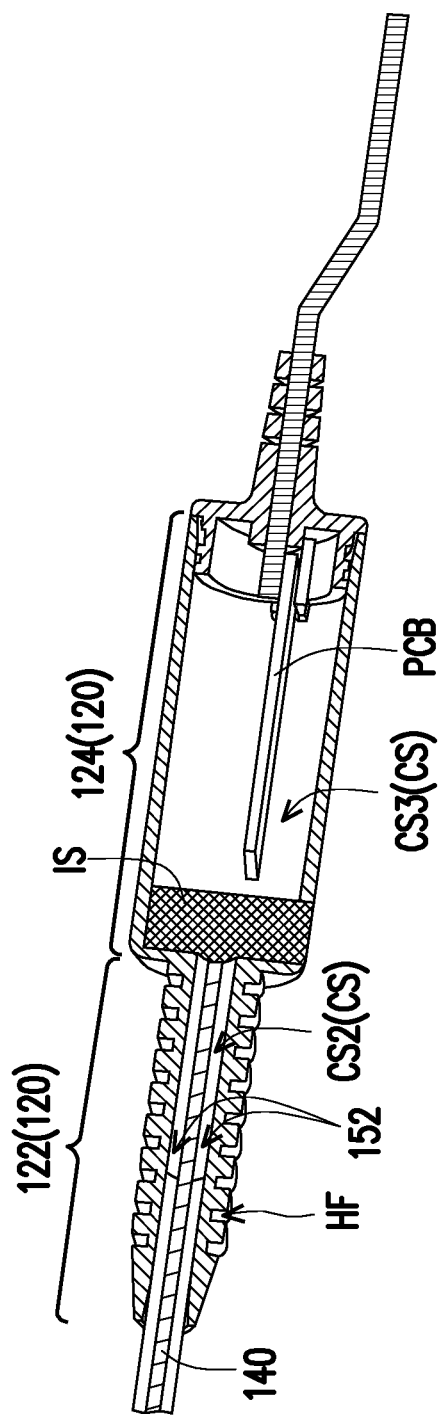

Referring to FIG. 3C, the embodiment is substantially similar to the embodiment of FIG. 3B, the main difference between the embodiment of FIG. 3C and the embodiment of FIG. 3B is as follows: the endoscopy system 100 may optionally include another heat-conductive material 152. The other heat-conductive material 152 is disposed in a portion of the connecting space CS2 of the front end portion 122 and located between the front end portion 122 and the heat pipe 140. The other heat-conductive material 152 is similar to the heat-conductive material 152 and will not be described in detail herein. By arrangement of the other heat-conductive material 152, the heat of the heat pipe 140 can be efficiently guided from the front end portion 122 to the outside. In addition, since the material of the front end portion 122 is, for example, metal, high-heat-conductive plastic or a combination thereof, and the heat-conductive material 152 is a substance in the form of plastic such as a heat-dissipating adhesive or heat-dissipating paste, namely, the front end portion 122 and the heat-conductive material 152 are heterogeneously combined with each other, if the first heat source 132 uses a high-power light emitting diode as required, or if the second heat source 134 uses a high-power image sensor as required, the materials of the front end portion 122 and the heat-conductive material 152 are matched in design, and then, the heat can be dissipated effectively. In addition, the appearance of the front end portion 122 may selectively use the design of a cooling fin structure HF to enhance heat dissipation efficiency. In addition, if the power of the heat sources 130 is low, the material of the front end portion may be selected to be a general plastic so as to reduce the manufacturing cost.

In other embodiments not shown, the medium between the front end portion 122 and the heat pipe 140 may also be air, and the invention is not limited thereto.

Figure 3D:
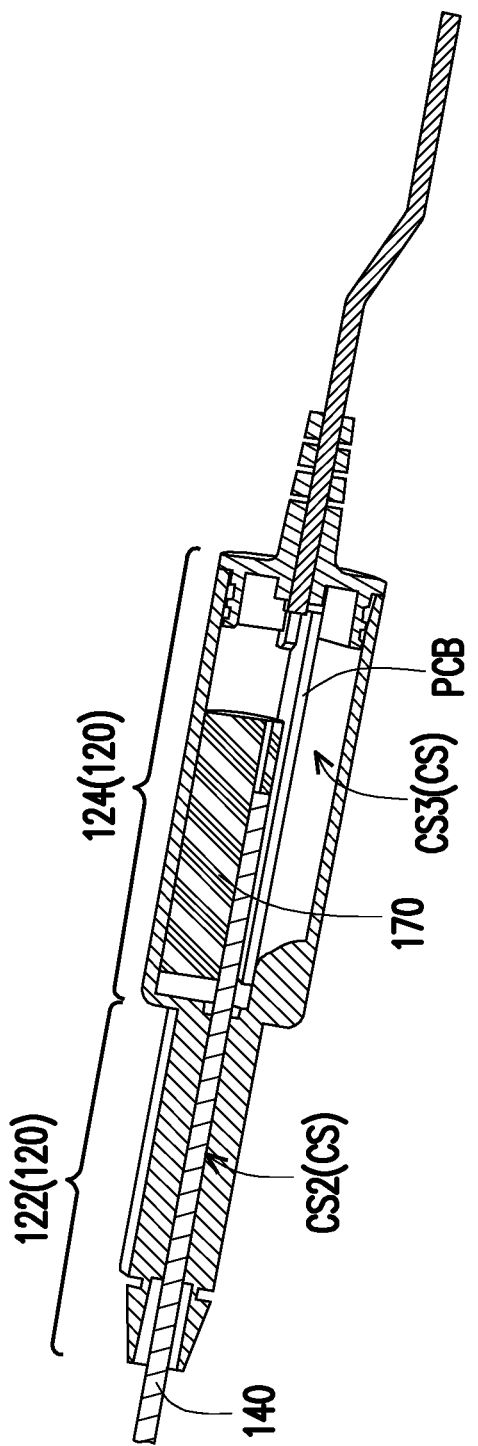

Referring to FIG. 3D, the endoscopy system 100 may optionally include a heat sink 170. The heat sink 170 is disposed in the connecting space CS3 of the handle segment 120. Thus, heat conducted by the heat pipe 140 can be rapidly dissipated by the heat sink 170 to the outside of the grip portion 124.

Figure 3E:
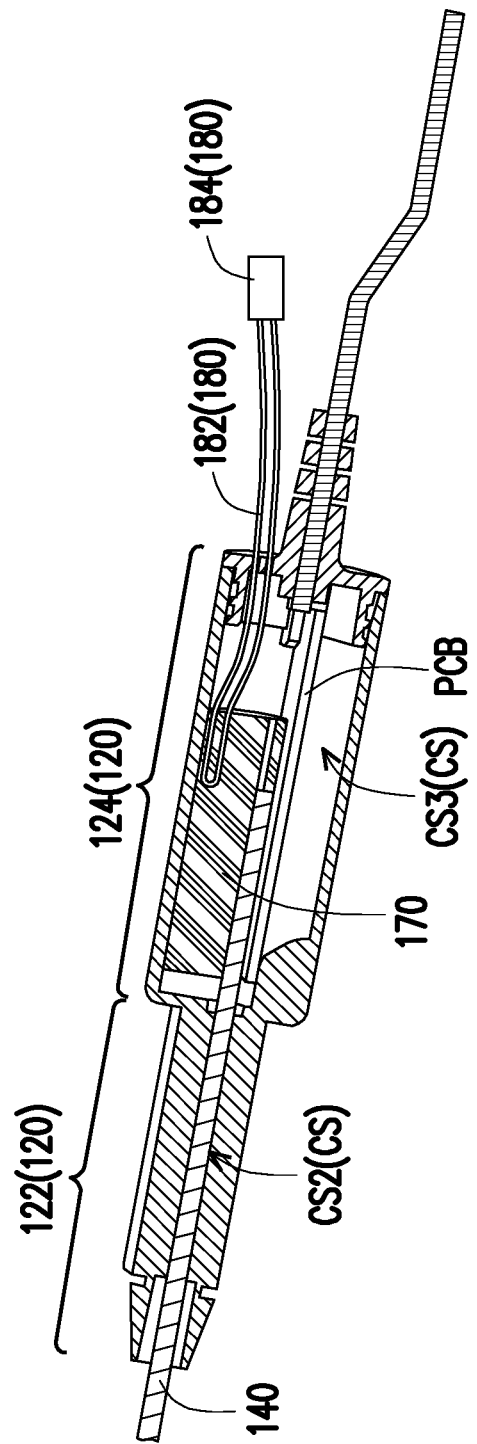

Referring to FIG. 3E, the embodiment is substantially similar to the embodiment of FIG. 3B, the main difference between the embodiment of FIG. 3E and the embodiment of FIG. 3B is as follows: the endoscopy system 100 may optionally further include a water cooling system 180. The water cooling system 180 includes a water pipe 182 and a pump 184. Water cooling fluid, such as, but not limited to, water, is contained within the water pipe 182, and the pump is configured to drive the water cooling fluid in the water pipe 182. The water pipe 182 of the water cooling system 180 is disposed in the connecting space CS3 of the grip portion 124 and communicates with the pump 184 by the water pipe 182. The water cooling system 180 is thermally coupled to the heat sink 170 and the grip portion 124 respectively. Therefore, by arrangement of the water cooling system 180, the water cooling fluid can quickly bring away the heat of the heat sink 170 so as to maintain the temperature of the heat sink 170 at a low temperature, and further maintain a large temperature difference between the heat sink 170 and the heat pipe 140, and heat can be dissipated quickly. In the present embodiment, the water pipe 182 is separated from a signal line C, for example, but in other embodiments, the water pipe 182 may also be disposed together with the signal line C, and the invention is not limited thereto.

In other embodiments, the heat sink 170 may optionally be omitted while only the water cooling system 180 is disposed, and the invention is not limited thereto.

Figure 3F:
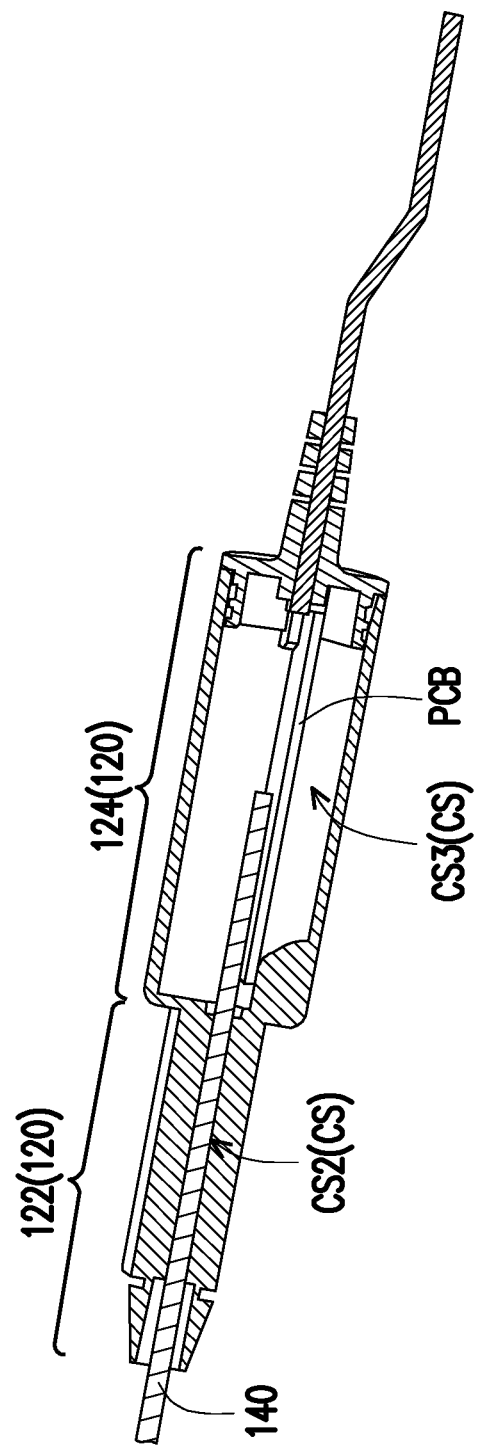

Referring to FIG. 3F, the embodiment is substantially similar to the embodiment of FIG. 3A, the main difference between the embodiment of FIG. 3F and the embodiment of FIG. 3A is as follows: the heat pipe 140 extends from a portion of the connecting space CS1 of the insertion tube segment 110, through the connecting space CS2 of the front end portion 122, to the connecting space CS3 of the handle segment 120. In the connecting space CS3 of the grip portion 124, the medium between the heat pipe 140 and the grip portion 124 is air. Thus, the heat conducted by the heat pipe 140 can be transferred to the outside of the grip portion 124 by natural heat dissipation.

In addition, in other embodiments not shown, the endoscopy system 100 may further include an insulator for insulating heat and electricity, and the material of the insulator may include a high-heat-resistance insulating material. The insulator is disposed in a portion of the connecting space CS1 in the insertion tube segment 110 and covers the at least one heat source 130 and the heat pipe 140. By the arrangement, heat can be prevented from being guided out directly from the first end portion E1 of the insertion tube segment 110 by the heat sources 130 to affect the physical condition of the patient, or from entering the heat pipe 140 from the outside. In addition, the high-heat-resistance insulating material is made of, for example, Teflon or polyethylene (PE), which can provide electrostatic protection for the heat sources 130 (electronic functional elements) and can also serve as an electrostatic protection material.

Figure 4A:
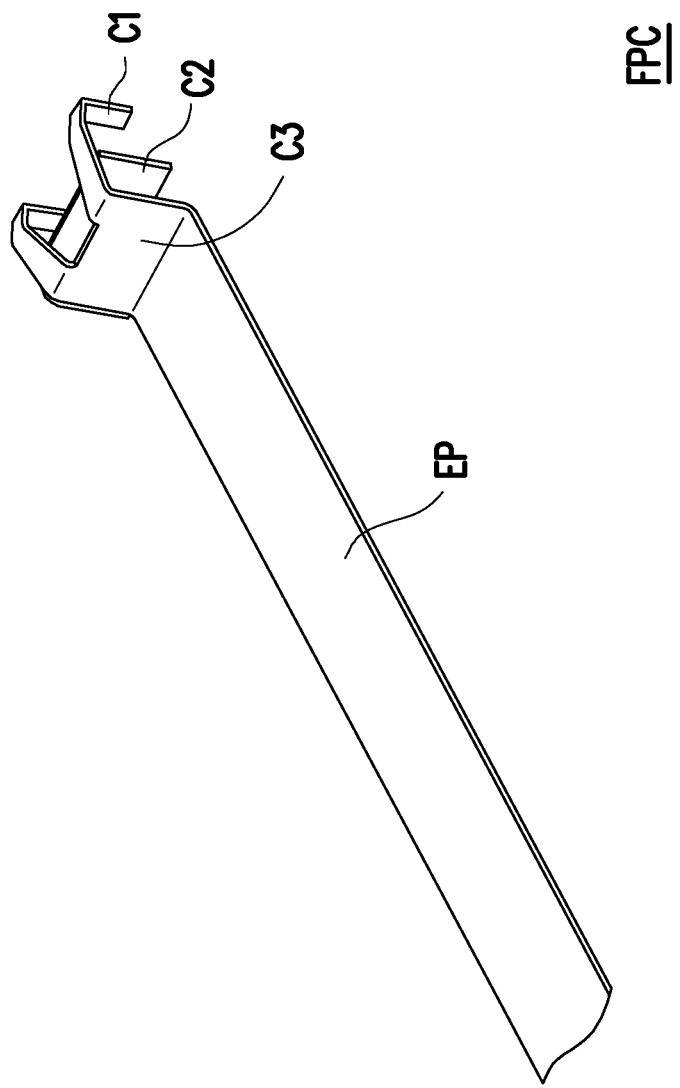
FIG. 4A is a schematic diagram of the appearance of a flexible printed circuit of FIG. 1.
Figure 4B:
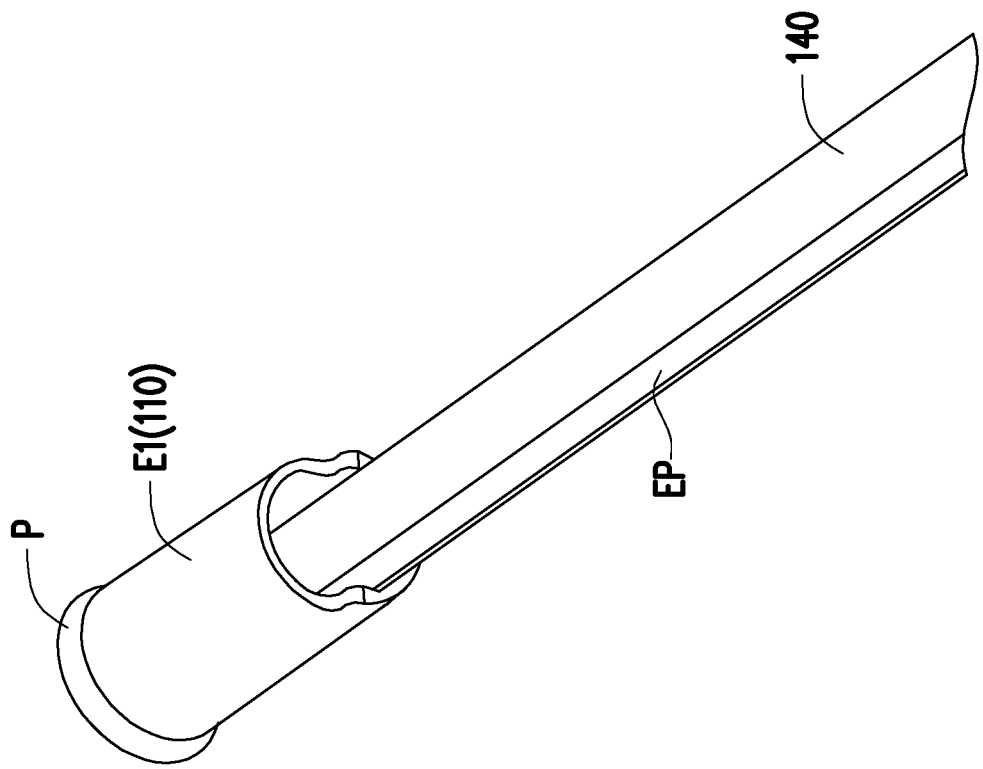
FIG. 4B is a partial schematic diagram of application of the flexible printed circuit of FIG. 4A to the endoscopy system.
Figure 4C:
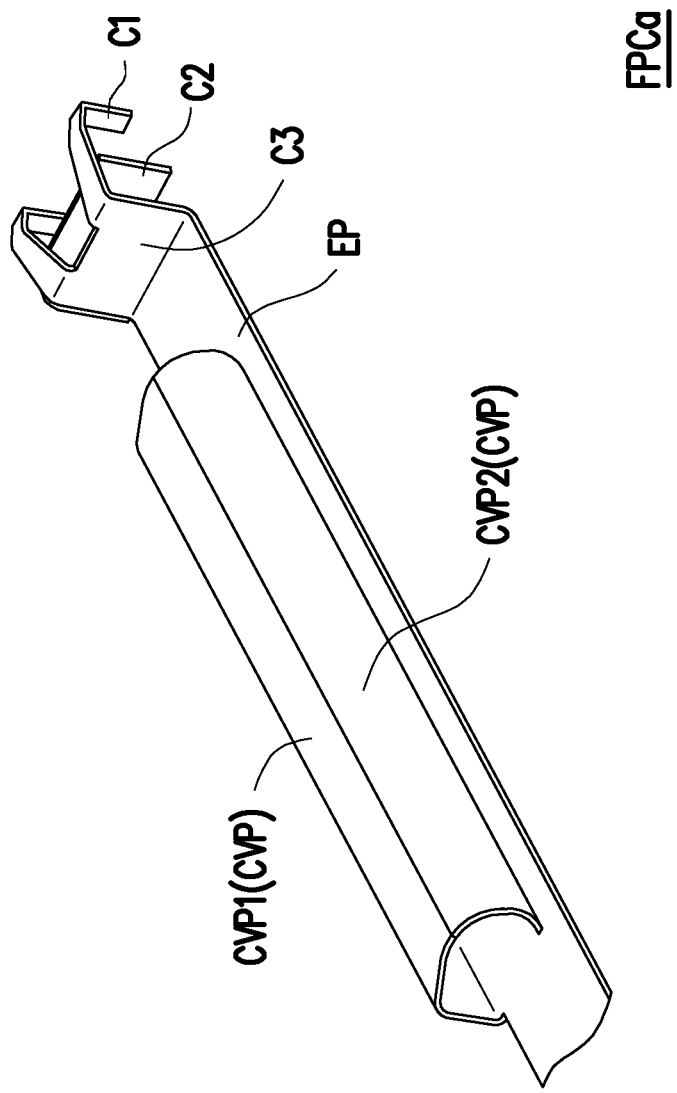
FIG. 4C is a schematic diagram of the appearance of the flexible printed circuit according to another embodiment of the invention.
Figure 4D:
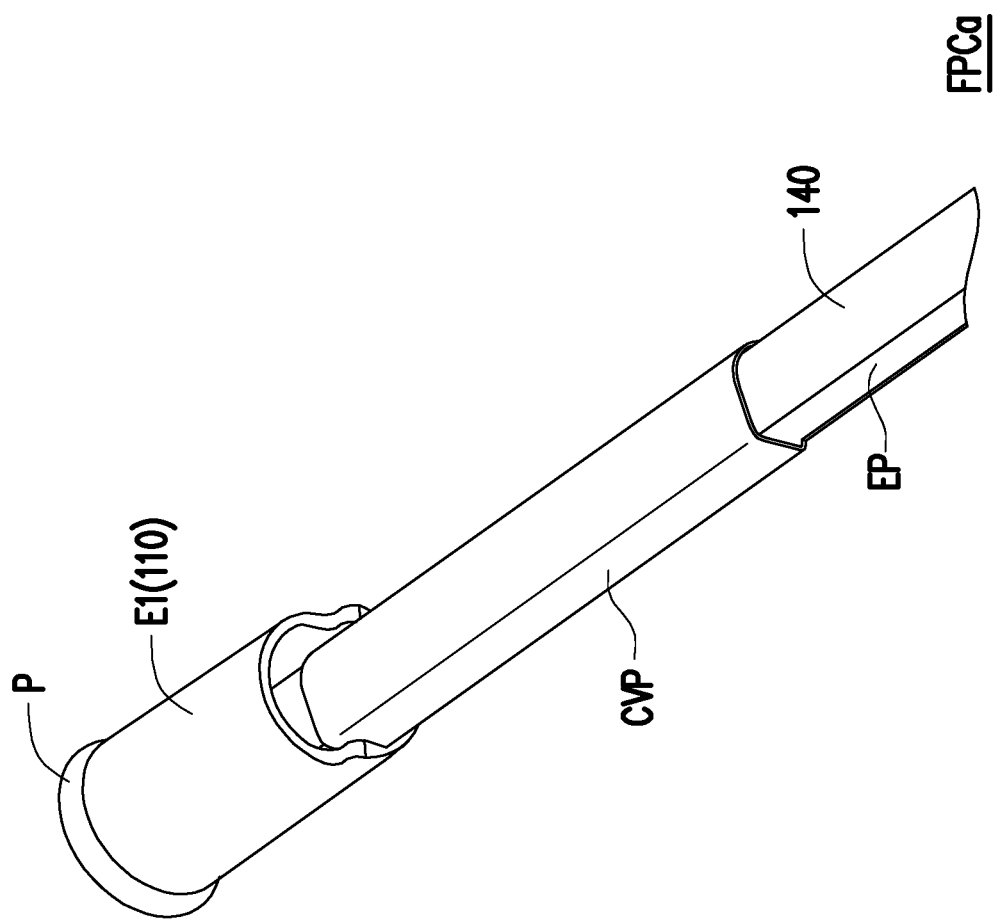
FIG. 4D is a partial schematic diagram of application of the flexible printed circuit of FIG. 4C to the endoscopy system.
Figure 4E:
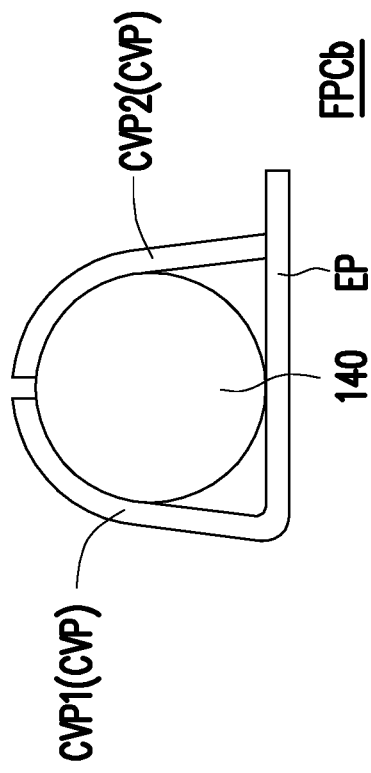
FIG. 4E and FIG. 4F are front schematic views of the flexible printed circuit in different embodiments.
Figure 4F:
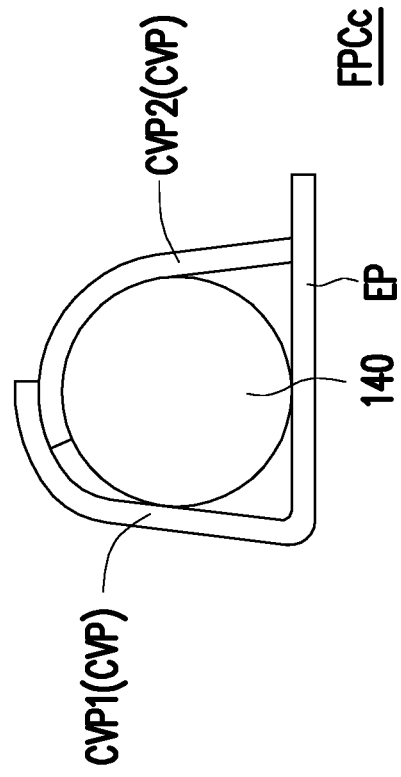

FIG. 4A is a schematic diagram of the appearance of the flexible printed circuit of FIG. 1. FIG. 4B is a partial schematic diagram of application of the flexible printed circuit of FIG. 4A to the endoscopy system. FIG. 4C is a schematic diagram of the appearance of the flexible printed circuit according to another embodiment of the invention. FIG. 4D is a partial schematic diagram of application of the flexible printed circuit of FIG. 4C to the endoscopy system. FIG. 4D and FIG. 4C are front schematic views of flexible printed circuits of different embodiments. FIG. 4E and FIG. 4F are front schematic views of flexible printed circuits of different embodiments.

Referring to FIG. 4A and FIG. 4B, the flexible printed circuit (FPC) of FIG. 4A only includes the extending portion EP. Referring to FIG. 4B, the extending portion EP at least extends from the connecting space CS1 of the first end portion E1 of the insertion tube segment 110 to a portion of the connecting space of the connecting portion (the connecting portion is not shown for clarity). In the present embodiment, the extending portion EP and the heat pipe 116 are in contact with each other. In other embodiments, the space between the extending portion EP and the heat pipe 116 is provided with the heat-conductive material 150, and the invention is not limited thereto.

Referring to FIG. 4C, a flexible printed circuit FPCa is substantially similar to the flexible printed circuit (FPC), and the main difference between the flexible printed circuit FPCa and the flexible printed circuit (FPC) is as follows: the flexible printed circuit FPCa may further include a covering portion CVP disposed on the extending portion EP of the flexible printed circuit FPCa. Specifically, the covering portion CVP includes first covering portions CVP1 and CVP2 which are connected with each other but are not overlapped with each other. Referring to FIG. 4D, the extending portion EP and the covering portion CVP together cover the heat pipe 140 and are in contact with the heat pipe 140. In other embodiments, the spaces among the extending portion EP, the covering portion CVP and the heat pipe 116 are provided with the heat-conductive material 150, and the invention is not limited thereto. Therefore, compared with the flexible printed circuit (FPC), the flexible printed circuit FPCa has the advantages that the extending portion EP can exchange heat with the heat pipe 140, furthermore, the covering portion CVP can exchange heat with the heat pipe 140, and by arrangement of the covering portion CVP, the area of heat conduction between the flexible printed circuit FPCa and the heat pipe 140 can be increased to improve the heat dissipation effect of the flexible printed circuit FPCa.

Referring to FIG. 4D, the flexible printed circuit FPCb of FIG. 4D is substantially similar to the flexible printed circuit FPCa of FIG. 4C, the main difference between the flexible printed circuit FPCb of FIG. D and the flexible printed circuit FPCa of FIG. 4C is as follows: the first covering portion CVP1 and the second covering portion CVP2 of the flexible printed circuit FPCb are separated from each other, and a gap is formed between the first covering portion CVP1 and the second covering portion CVP2 of the flexible printed circuit FPCb to expose part of the heat pipe 140.

Referring to FIG. 4E, the flexible printed circuit FPCc of FIG. 4E is substantially similar to the flexible printed circuit FPCa of FIG. 4C, and the main difference between the flexible printed circuit FPCc of FIG. 4E and the flexible printed circuit FPCa of FIG. 4C is as follows: the first covering portion CVP1 and the second covering portion CVP2 of the flexible printed circuit FPCb are overlapped with each other.

Figure 5:
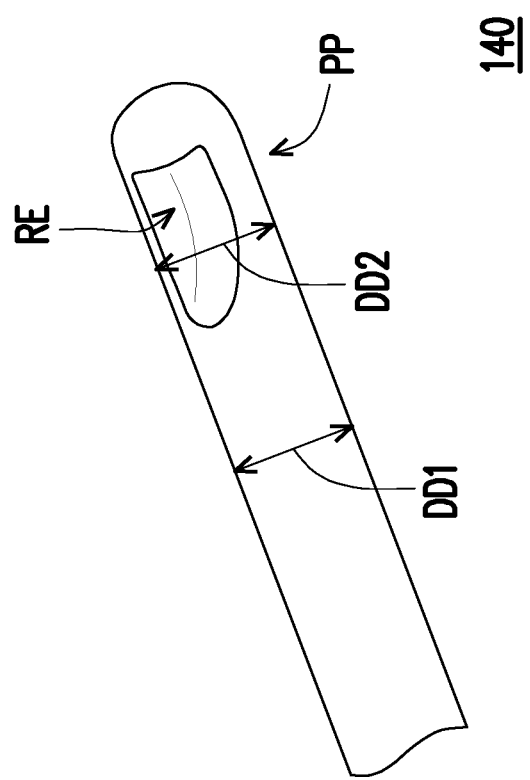
FIG. 5 is a schematic view of the appearance of an end portion of a heat pipe according to an embodiment of the invention.

FIG. 5 is a schematic view of the appearance of an end portion of a heat pipe according to an embodiment of the invention.

Referring to FIG. 5, in this embodiment, the heat pipe 140 includes an end portion PP close to the handle segment 120, the end portion PP has a recess RE, and an outer diameter DD1 at the recess RE is substantially equal to an outer diameter DD2 at the remaining part of the heat pipe 140. When the heat pipe 140 is assembled to the handle segment 120 by the end portion PP, this design can avoid assembly difficulty resulting from an excessively large outer diameter D1 and can avoid interference with other parts inside the handle segment 120.

Based on the foregoing, in the endoscopy system of the embodiment of the invention, since the heat sources are disposed at the first end portion of the insertion tube segment, the heat-conductive material is disposed between the first end portion and the heat sources and thermally coupled to the heat pipe in such a manner that the heat pipe extends from the connecting space in the insertion tube segment to the connecting space of the handle segment. When the heat sources radiate heat due to the execution of the function of the heat sources, the heat can be quickly transferred to the heat pipe by the heat-conductive material, and the heat can be guided from the first end portion of the insertion tube segment closer to the patient to the handle segment further away from the patient, and besides achievement of the rapid heat dissipation effect, influences of heating of the heat sources to the patient can be reduced.

What is claimed is:

1. An endoscopy system comprising:
   an insertion tube segment comprising a first end portion and a second end portion opposite to each other;
   a handle segment, the insertion tube segment being inserted into the handle segment,
   wherein an inside of the insertion tube segment and an inside of the handle segment commonly comprise a connecting space;
   at least one heat source disposed at the first end portion of the insertion tube segment;
   a heat pipe disposed in the connecting space and at least extending from a portion of the connecting space of the insertion tube segment to a portion of the connecting space of the handle segment; and
   a heat-conductive material disposed between the at least one heat source and the first end portion of the insertion tube segment and thermally coupled to the at least one heat source and the heat pipe, respectively,
   wherein the at least one heat source is multiple in number and an electronic functional element, one of the at least one heat source comprises a flexible printed circuit, and the flexible printed circuit comprises a first carrying portion, a second carrying portion, a third carrying portion, and an extending portion,
   wherein the first carrying portion, the second carrying portion, and the third carrying portion are connected with one another, and the extending portion is connected to the third carrying portion,
   wherein at least one of the first carrying portion and the second carrying portion is configured to carry and thermally coupled to another one of the at least one heat source,
   wherein the extending portion at least extends from a portion of the connecting space of the first end portion of the insertion tube segment to a portion of the connecting space of a connecting portion of the insertion tube segment,
   wherein the extending portion and the heat pipe are in contact with each other,
   wherein a space between the extending portion and the heat pipe is provided with the heat-conductive material,
   wherein the heat-conductive material is thermally coupled to the extending portion and the heat pipe, respectively,
   wherein the handle segment further comprises a front end portion and a grip portion, the front end portion clamps the second end portion of the insertion tube segment, and at least one portion of the insertion tube segment is overlapped with the front end portion,
   wherein the heat pipe extends from the portion of the connecting space of the insertion tube segment, through a portion of the connecting space of the front end portion, to a portion of the connecting space of the grip portion.

2. The endoscopy system according to claim 1, further comprising a thermal insulator disposed between a portion of the connecting space of the front end portion and a portion of the connecting space of the grip portion.

3. The endoscopy system according to claim 1, further comprising another heat-conductive material disposed in a portion of the connecting space of the front end portion and positioned between the front end portion and the heat pipe.

4. The endoscopy system according to claim 1, wherein in the connecting space of the front end portion, a medium between the heat pipe and the front end portion is air.

5. The endoscopy system according to claim 1, wherein an appearance of the front end portion comprises a cooling fin structure.

6. The endoscopy system according to claim 1, wherein in the connecting space of the grip portion, a medium between the heat pipe and the grip portion is air.

7. The endoscopy system according to claim 1, further comprising a heat sink disposed in the connecting space of the grip portion and positioned between the heat pipe and the grip portion.

8. The endoscopy system according to claim 7, further comprising a water cooling system disposed in the connecting space of the grip portion, communicating with outside, and thermally coupled to the heat sink and the grip portion, respectively.

9. The endoscopy system according to claim 1, wherein the flexible printed circuit further comprises a covering portion, the covering portion is disposed on the extending portion, and the extending portion and the covering portion commonly cover the heat pipe.

10. The endoscopy system according to claim 1, wherein the heat-conductive material comprises a heat-conductive adhesive or heat-conductive paste.

11. The endoscopy system according to claim 1, further comprising a protective element disposed at the first end portion of the insertion tube segment and configured to cover the at least one heat source.

12. The endoscopy system according to claim 1, further comprising an insulator disposed in a portion of the connecting space in the insertion tube segment and covering the at least one heat source and the heat pipe.

13. The endoscopy system according to claim 1, wherein a material of the handle segment comprises metal, a high-heat-conductive material or a combination thereof.

14. The endoscopy system according to claim 1, wherein an outer diameter of an end portion of the heat pipe close to the handle segment is substantially equal to an outer diameter of a remaining part of the heat pipe, and the end portion has a recess.

15. An endoscopy system comprising:
   an insertion tube segment comprising a first end portion and a second end portion opposite to each other;
   a handle segment, the insertion tube segment being inserted into the handle segment,
   wherein an inside of the insertion tube segment and an inside of the handle segment commonly comprise a connecting space;
   at least one heat source disposed at the first end portion of the insertion tube segment; and
   a heat pipe disposed in the connecting space and at least extending from a portion of the connecting space of the insertion tube segment to a portion of the connecting space of the handle segment,
   wherein the handle segment further comprises a front end portion and a grip portion, the front end portion clamps the second end portion of the insertion tube segment, and at least one portion of the insertion tube segment is overlapped with the front end portion, and
   wherein the heat pipe extends from the portion of the connecting space of the insertion tube segment, through a portion of the connecting space of the front end portion, to a portion of the connecting space of the grip portion.

16. The endoscopy system according to claim 15, further comprising a heat-conductive material disposed between the at least one heat source and the first end portion of the insertion tube segment and thermally coupled to the at least one heat source and the heat pipe, respectively.

17. The endoscopy system according to claim 15, wherein an appearance of the front end portion comprises a cooling fin structure.

18. The endoscopy system according to claim 15, further comprising a heat sink disposed in the connecting space of the grip portion and positioned between the heat pipe and the grip portion.

19. The endoscopy system according to claim 18, further comprising a water cooling system disposed in the connecting space of the grip portion, communicating with outside, and thermally coupled to the heat sink and the grip portion, respectively.

* * * * *